United States Patent
Baudys et al.

(12)

(10) Patent No.: US 6,465,694 B1
(45) Date of Patent: Oct. 15, 2002

(54) METHOD FOR PREPARATION OF POLYETHYLENE GLYCOL ALDEHYDE DERIVATIVES

(75) Inventors: Miroslav Baudys; Feng Liu; Sung Wan Kim, all of Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 09/830,470

(22) PCT Filed: Oct. 26, 1999

(86) PCT No.: PCT/US99/25174

§ 371 (c)(1),
(2), (4) Date: Jun. 4, 2001

(87) PCT Pub. No.: WO00/24697

PCT Pub. Date: May 4, 2000

Related U.S. Application Data

(60) Provisional application No. 60/105,630, filed on Oct. 26, 1998.

(51) Int. Cl.[7] .................. C07C 43/10; C07C 47/12; C07C 321/14
(52) U.S. Cl. .......................... 568/494; 568/41
(58) Field of Search ............... 532/44; 568/41, 568/494

(56) References Cited

U.S. PATENT DOCUMENTS

| 5,252,714 A | 10/1993 | Harris et al. |
| 5,510,418 A | 4/1996 | Rhee et al. |

FOREIGN PATENT DOCUMENTS

| EP | 0 372 752 A2 | 11/1989 |

OTHER PUBLICATIONS

J. Milton Harris, et al.—Poly(ethylene glycols) as Soluble, Recoverable, Phase–Transfer Catalysts—J. Org. Chem. 1982, 47, 4789–4791.

I.E. Marko et al., Copper–catalyzed oxidation of alcohols to aldehydes and ketones: an efficient, aerobic alternative; Science 1996, 274, 2044–2046 (abstract CAPLUS 126:103888).

*Primary Examiner*—Michael Borin
(74) *Attorney, Agent, or Firm*—Clayton, Howarth & Cannon, P.C.

(57) ABSTRACT

Aldehyde derivatives of polyethylene glycols and methods of making thereof are disclosed. These aldehyde derivatives can be used to make polyethylene glycol-hydrazines, polyethylene glycol-thiols, polyethylene glycol amines, and branched polyethylene glycols. PEG aldehyde derivatives or other functional PEG derivatives prepared from PEG aldehydes are useful for protein conjugation and surface modification.

12 Claims, No Drawings

METHOD FOR PREPARATION OF POLYETHYLENE GLYCOL ALDEHYDE DERIVATIVES

CROSS-REFERENCE TO RELATED APPLICATIONS

This application claims the benefit of U.S. Provisional Application No. 60/105,630, filed Oct. 26, 1998, which is hereby incorporated by reference.

BACKGROUND OF THE INVENTION

The present invention relates to a direct, very mild, efficient method of synthesis of derivatives of polyethylene glycol having one or more terminal aldehyde groups and the use of these derivatives as reagents for modifying peptides or proteins and for the preparation of other types of functionalized polyethylene glycols.

In the last decade, enormous progress in recombinant DNA technology enabled discovery and/or production of a large number of physiologically active proteins, many of them having unforeseen potential to be used as biopharmaceuticals. Unfortunately, most of these peptides and proteins exhibit very fast plasma clearance, thus requiring frequent injections to ensure steady pharmaceutically relevant blood levels of a particular peptide or protein with pharmacological activity. Further, many pharmaceutically relevant peptides and proteins, even those having human primary structure, can be immunogenic, giving rise to production of neutralizing antibodies circulating in the bloodstream. This is especially true for intravenous and subcutaneous administration, which is of particular concern for most peptide and protein drugs.

To solve these problems, various hydrophilic macromolecular compounds have been conjugated with peptide and protein drugs. This has proven to be very efficient and useful in decreasing the immunogenicity and increasing the circulatory half-life of peptide and protein drugs. Among hydrophilic macromolecular compounds, polyethylene glycol derivatives have been used most frequently for synthesis of peptide and protein conjugates, because such derivatives are non-immunogenic and very hydrophilic, and thus do not affect the three dimensional structure (folding) of protein drugs. Moreover, dynamic polyethylene chains also provide protection against hydrolytic degradation by proteolytic enzymes.

To achieve significant level of modification of peptides and proteins with polyethylene glycol (PEG) derivatives, several methods of activation have been widely used, such as the triazine method (F. F. Davis et al., U.S. Pat. No. 4,179,337), the active ester method with N-hydroxysuccinimide (F. Veronese et al., U.S. Pat. No. 5,286,637), and the direct activation method with carbonyldiimidazole (G. S. Bethell et al., 254 J. Biol. Chem. 2572–2574 (1979)). Typically, these activated PEG derivatives contain an electrophilic center that is available for reaction with nucleophilic centers on peptides and proteins, such as amino groups. The common disadvantage of these derivatives is instability in aqueous media against nonspecific hydrolysis at alkaline pH, where the modification reaction usually takes place. Recently, attachment of PEG chains to peptides and proteins via reductive alkylation has been described (P. Wirth et al., 19 Bioorg. Chem. 133–142 (1991); S. M. Chamow et al., 5 Bioconjugate Chem 133–140 (1994); O. B. Kinstler et al., 13 Pharm. Res. 996–1002 (1996)). This method requires introduction of an aldehyde group at the end of a monomethoxypolyethylene glycol (MePEG) chain that originally carried a hydroxyl group. Contrary to other activated PEG derivatives mentioned above, PEG-aldehydes, like aldehydes in general, are mostly inert to water and react selectively with the amino groups of peptides and proteins as nucleophiles in aqueous media. These two properties are highly desirable, not only because of stability upon long-term storage, but also because of high selectivity for coupling of these aldehyde-PEG derivatives and for simplicity.

Originally, MePEG was oxidized with active $MnO_2$ to yield MePEG-ethanal (acetaldehyde) as described in U.S. Pat. No. 4,002,531 for attaching PEG chains to enzymes and other proteins. This procedure was later shown to be very inefficient by M. S. Paley & J. M. Harris, 25 J. Polym. Sci. Polym. Chem. Edn. 2447–2454 (1987). Thus, other oxidative methods, such as the Moffatt procedure, were introduced as described by Harris et al., 22 J. Polym. Sci. Polym. Chem. Edn. 341–352 (1984). These oxidative reactions, however, are not quantitative and may be accompanied by unwanted side reactions and/or MePEG chain cleavage. Further, product purification is difficult. In parallel, a more gentle and quantitative alkylation method using β-bromopropionaldehyde has been used to prepare MePEG-aldehyde derivatives (J. M. Harris & M. R.-Sedaghat-Herati, U.S. Pat. No. 5,252,714). A terminal ethyl spacer was introduced to increase the stability of MePEG aldehyde derivatives in water in the presence of base since it was argued, on the basis of $CH_3$—O—$CH_2$—$CH_2$—O—$CH_2$—CHO chemical stability data (M. S. Paley & J. M. Harris, 25 J. Polym. Sci. Polym. Chem. Edn. 2447–2454 (1987)), that MePEG-ethanal derivatives are unstable in water in the presence of base. To the contrary, MePEG-ethanal derivatives were successfully used for protein modification when used in 20 to 200 molar excess (PEG derivative/Protein molar ratio) at pH 7.0–8.0 (P. Wirth et al., 19 Bioorg. Chem. 133–142 (1991); S. M. Charnow et al., 5 Bioconjugate Chem 133–140 (1994); O. B. Kinstler et al., 13 Pharm. Res. 996–1002 (1996)).

A new catalytic, oxidative method for conversion of alcohols into carbonyl compounds utilizing oxygen or even air as the ultimate and stoichiometric oxidant, producing water as the only byproduct, has been recently discovered and described by I. E. Marko et al., 274 Science 2044–2046 (1996). The active catalyst appears to be heterogeneous, absorbed on insoluble $K_2CO_3$, and is composed of CuCl, diethylazodicarboxylate or the corresponding hydrazine, and 1,10-phenanthroline. Apolar solvents such as benzene or toluene are required. $K_2CO_3$, besides its role as a solid support, also acts as a base and as a water scavenger, but can be replaced by 4 Å molecular sieves and a catalytic amount of nonoxidizable base, such as $KOBu^t$. This process is very efficient under mild conditions (temp. 70–90° C.), providing high degrees of conversion (80–100%), and is not only economically viable but it is also environmentally friendly.

In view of the foregoing, it will be appreciated that providing an efficient, gentle method for preparation of polyethylene glycol aldehyde derivatives would be a significant advancement in the art.

BRIEF SUMMARY OF THE INVENTION

An object of the present invention is to provide a method of preparation of PEG-dialdehydes and alkoxyPEG (i.e., RO-PEG) aldehydes and their homologues that retain reactivity in water and selectively react with amino groups.

Another object of the invention is to provide PEG-dialdehydes and RO-PEG-aldehydes and their homologuestat react selectively with amino groups and are stable in water.

Yet another object of the invention is to provide bifunctional PEG and monofunctional RO-PEG derivatives and their homologues that can be prepared starting from PEG-dialdehydes and RO-PEG-aldehydes or their homologues.

Still another object of this invention is the process of preparation of bifunctional PEG and monofunctional RO-PEG derivatives and their homologues starting from PEG-dialdehydes and RO-PEG-aldehydes or their homologues.

These and other objects can be addressed by providing compositions, methods of making thereof, and methods of using thereof. An illustrative embodiment of the invention relates to the oxidation of polyethylene glycol derivatives having the formula:

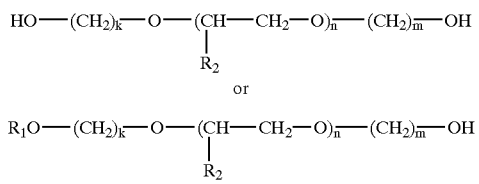

wherein $R_1$ represents lower alkyl, $R_2$ represents lower alkyl or H, n is an integer from about 3 to about 500, and k and m are integers from about 2 to about 12, utilizing a catalytic procedure that provides high yields of corresponding PEG-dialdehyde derivatives and RO-PEG-aldehyde derivatives having the formula:

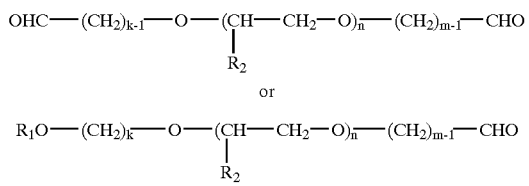

and enables their preparation and isolation in the absence of water.

Another illustrative embodiment of the invention relates to aldehyde derivatives of polyethylene glycos of the formula:

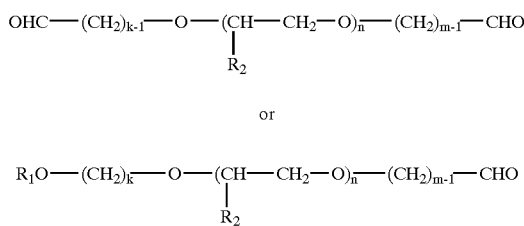

wherein $R_1$ represents lower alkyl, $R_2$ represents lower alkyl or H, n is an integer from about 3 to about 500, and k and m are integers from about 4 to about 12.

Still another embodiment of the invention relates to polyethylene glycol derivatives of the formula:

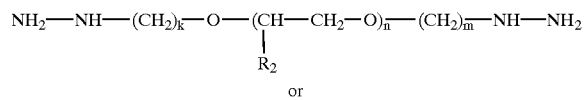
or

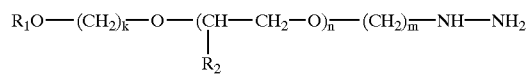

wherein $R_1$ represents lower alkyl, $R_2$ represents lower alkyl or H, n is an integer from about 3 to about 500, and k and m are integers from about 2 to about 12.

Yet another illustrative embodiment of the invention relates to polyethylene glycol derivatives of formula:

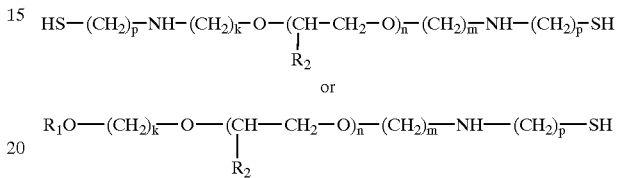

wherein $R_1$ represents lower alkyl, $R_2$ represents lower alkyl or H, n is an integer from about 3 to about 500, k and m are integers from about 2 to about 12, and p is an integer from about 2 to about 12.

A further illustrative embodiment of the invention relates to methods of preparation of the polyethylene glycol derivatives summarized above. Thus, PEG-dihydrazine derivatives and RO-PEG-hydrazine derivatives are prepared by reacting a particular PEG-dialdehyde derivative or RO-PEG-aldehyde derivative with hydrazine in the presence of reducing agent such as $NaBH_3CN$ or $NaBH_4$. Also, PEG-dithiol derivatives and RO-PEG-thiol derivatives can be synthesized from a particular PEG-dialdehyde derivative or RO-PEG-aldehyde derivative and selected mercaptoalkylamine in the presence of reducing agent such as $NaBH_3CN$ or $NaBH_4$.

A still further embodiment of the invention relates to branched polyethylene glycol derivatives of the formula:

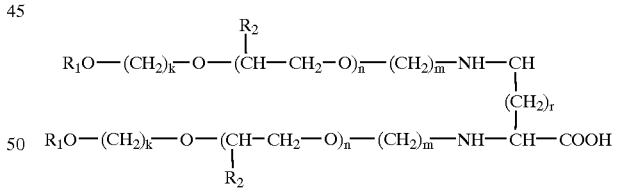

wherein $R_1$ represents lower alkyl, $R_2$ represents lower alkyl or H, n is an integer from about 3 to about 500, k and m are integers from about 2 to about 12, and r is an integer from 0 to about 5. These branched polyethylene glycol derivatives are prepared by reacting a particular RO-PEG-aldehyde derivative with a selected diaminocarboxylic acid, which does not necessarily have to be an α-acarboxylic acid as shown in the formula but also can be β-, γ-, or δ-carboxylic acid, in the presence of reducing agent such as $NaBH_3CN$ or $NaBH_4$.

Another illustrative embodiment of the invention relates to branched polyethylene glycol derivatives of the formula:

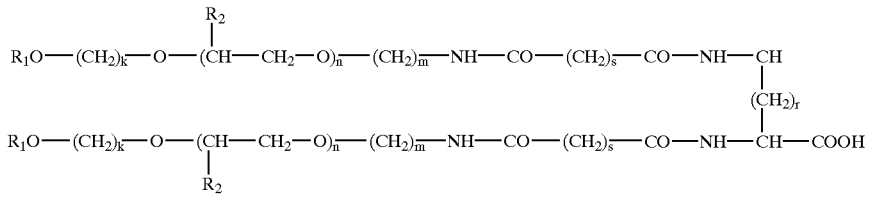

wherein $R_1$ represents lower alkyl, $R_2$ represents lower alkyl or H, n is an integer from about 3 to about 500, k and m are integers from about 2 to about 12, r is an integer from 0 to about 5, and s is 2 or 3. This type of branched polyethylene glycol derivative is prepared starting from monoaminoPEG derivatives, as set forth below, and reacting them with dicarboxylic acid cyclic anhydrides, thus converting monoaminoPEG derivatives into monocarboxyPEG derivatives. A selected activated monocarboxyPEG derivative is then reacted with a selected diaminocarboxylic acid, which does not necessarily have to be an a-carboxylic acid but can also be β-, γ-, or δ-carboxylic, yielding a branched polyethylene glycol derivative as specified by the general formula above.

Finally, another illustrative embodiment of the invention relates to methods of preparation of amino-PEG derivatives of the formula:

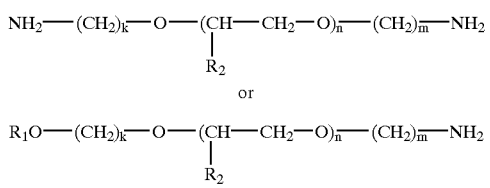

wherein $R_1$ represents lower alkyl, $R_2$ represents lower alkyl or H, n is an integer from about 3 to about 500, and k and m are integers from about 3 to about 12. These derivatives can be synthesized by reductive amination of corresponding PEG-dialdehyde derivatives or RO-PEG-aldehyde derivatives, prepared as disclosed above, with ammonium salt in the presence of reducing agent such as $NaBH_3CN$ or $NaBH_4$.

DETAILED DESCRIPTION

Before the present polyethylene glycol aldehydes, derivatives thereof, and methods for making thereof are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

The publications and other reference materials referred to herein to describe the background of the invention and to provide additional detail regarding its practice are hereby incorporated by reference. The references discussed herein are provided solely for their disclosure prior to the filing date of the present application. Nothing herein is to be construed as an admission that the inventors are not entitled to antedate such disclosure by virtue of prior invention.

It must be noted that, as used in this specification and the appended claims, the singular forms "a," "an," and "the" include plural referents unless the context clearly dictates otherwise. Thus, for example, reference to "an apolar solvent" includes a mixture of two or more apolar solvents, reference to "a catalyst" includes reference to one or more of such catalysts, and reference to "a polyethylene glycol" includes reference to a mixture of two or more polyethylene glycols.

In describing and claiming the present invention, the following terminology will be used in accordance with the definitions set out herein.

As used herein, "comprising," "including," "containing," "characterized by," and grammatical equivalents thereof are inclusive or open-ended terms that do not exclude additional, unrecited elements or method steps. "Comprising" is to be interpreted as including the more restrictive terms "consisting of" and "consisting essentially of."

As used herein, "consisting of" and grammatical equivalents thereof exclude any element, step, or ingredient not specified in the claim.

As used herein, "consisting essentially of" and grammatical equivalents thereof limit the scope of a claim to the specified materials or steps and those that do not materially affect the basic and novel characteristic or characteristics of the claimed invention.

As used herein, "peptide" means peptides of any length and includes proteins. The terms "polypeptide" and "oligopeptide" are used herein without any particular intended size limitation, unless a particular size is otherwise stated. Typical of peptides that can be utilized are those selected from group consisting of oxytocin, vasopressin, adrenocorticotrophic hormone, epidermal growth factor, prolactin, luliberin or luteinising hormone releasing hormone, growth hormone, growth hormone releasing factor, insulin, somatostatin, glucagon, interferon, gastrin, tetragastrin, pentagastrin, urogastrone, secretin, calcitonin, enkephalins, endorphins, angiotensins, renin, bradykinin, bacitracins, polymixins, colistins, tyrocidin, gramicidins, and synthetic analogues, modifications and pharmacologically active fragments thereof, monoclonal antibodies and soluble vaccines. The only limitation to the peptide or protein that may be utilized is one of functionality.

In the present specification, the lower alkyl groups represented by R, $R_1$, and $R_2$ may be either straight or branched, preferably lower alkyl groups having 1 to 4 carbon atoms such as methyl, ethyl, n-propyl, isopropyl, n-butyl, isobutyl, and the like. Polyethylene glycol derivatives and monoalkoxypolyethylene glycol derivatives of the formula:

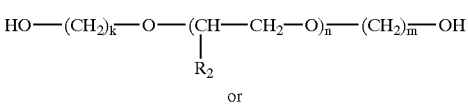

or

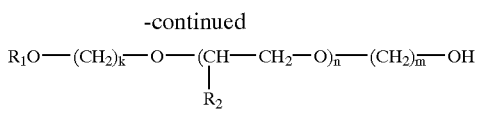

wherein $R_1$ is lower alkyl, $R_2$ is lower alkyl or H, n is an integer from about 3 to about 500, and k and m are integers from about 2 to about 12, can be easily produced by some of the well-known methods in the art. These PEG derivatives or their homologues are dissolved in an apolar solvent such as benzene or, preferably, toluene, and 2 equivalents of $K_2CO_3$ for each hydroxyl group are added. Also, an effective amount of a catalyst should be added to the reaction mixture. By "effective amount" is meant an amount sufficient to increase the rate of reaction. Such an effective amount can be determined as a matter of routine by a person skilled in the art. Preferably, the amount of catalyst added to the reaction is about 1 to about 10 mol %, more preferably about 5 mol %, with regard to hydroxyl groups. The catalyst comprises (i) a transition metal cation having two main oxidative states, (ii) an aromatic heterocycle containing nitrogen, and (iii) a member selected from the group consisting of diethylazodicarboxylate, a hydrazine derivative of diethylazodicarboxylate, and tert-butyl analogs thereof. The transition metal cation having two main oxidative states is preferably a member selected from the group consisting of $Cu^+$, $Co^{2+}$, $Fe^{2+}$, $Ni^{2+}$, and mixtures thereof. More preferably, the transition metal cation is $Cu^+$. Preferred aromatic heterocycles containing nitrogen include 1,10-phenanthroline and $\alpha,\alpha'$-dipyridyl. Preferably, the member selected from the group consisting of diethylazodicarboxylate, a hydrazine derivative of diethylazodicarboxylate, and tert-butyl analogs thereof is diethylazodicarboxylate. An especially preferred catalyst comprises CuCl (cuprous chloride), 1,10-phenanthroline, and diethylazodicarboxylate. The catalyst is added to the mixture, and $O_2$ or air (aerobic conditions) is bubbled through the mixture with the temperature of the mixture in the range of about 40° C. to about 90° C. It is also noteworthy that catalyst deactivation is not observed and insoluble catalyst, which can easily be separated from the rest of reaction mixture, can be recycled and repetitively used in a new reaction. With respect to the composition of the catalyst, $Cu^+$ can be replaced by other transient metal cations having two main oxidative states, such as $Co^{2+}$, $Fe^{2+}$, or $Ni^{2+}$. Phenanthroline can be replaced by other aromatic heterocycles containing nitrogen such as $\alpha,\alpha'$-dipyridyl. Diethylazodicarboxylate or its hydrazine derivative can be replaced by corresponding tert-butyl analogs, which remarkably improve the rate of the reaction and the lifetime of catalyst (I. E. Marko et al., 274 Science 2044–2046 (1996)).

The reaction can be described as follows:

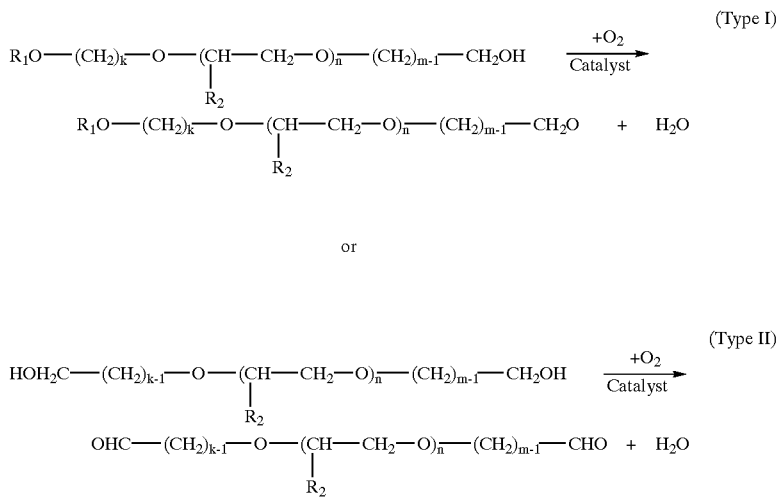

wherein $R_1$ is lower alkyl, $R_2$ is lower alkyl or H, n is an integer of about 3 to about 500, and k and m are integers of about 2 to about 12. After completion of the reaction and removal of catalyst by filtration, the PEG-aldehyde derivative product can be easily purified and recovered at room temperature by precipitation in dry ether and filtration of the solid product, which can be stored in a stable solid form until use. For low molecular weight PEG-aldehyde derivatives (600 or lower), the same precipitation procedure can be used. In this case, however, the precipitating ether medium has to be kept at −20° C., and the precipitated PEG-aldehyde derivative is separated by centrifugation at −20° C.

Type I PEG-aldehyde derivatives are ideal for protein modification because the reaction involved, reductive amination, is highly selective for amino groups. Reductive amination is well known in the art, and can be described by the formula PEG-CHO+$NH_2$—R'→PEG-CH—NHR'. E.g, R. T. Morrison & R. N. Boyd, Organic Chemistry 735, 740741 ($3^{rd}$ ed., 1973). The reductive amination reaction can be easily performed in water because the RO-PEG-aldehyde derivatives exhibit substantial stability as compared to other activated PEG derivatives for protein modification, and the extent of the reaction can also be controlled such that partial modification is possible. The last goal is achieved by varying the molar ratio of protein to RO-PEG-aldehyde derivative (usually 5 to 50 molar excess) and/or pH of the coupling reaction which can Be kept in the range from pH 5.0 to 9.0. Using slightly acidic conditions (pH 5.0–6.0) for coupling, it is possible to selectively target the N-terminal amino groups of peptides or proteins, since the ε-amino groups on lysine residues do not react under these conditions because they are fully protonated. Concomitantly, RO-PEG-aldehyde derivatives are stable and reactive under slightly acidic conditions. Another advantage of the reductive amination method for PEG chain attachment is that it preserves the overall charge when primary amino groups are converted into secondary amino groups.

Type II PEG-aldehyde derivatives can be used for protein immobilization. In this case, a PEG-dialdehyde derivative is first coupled to an amino-group-modified surface in water. Excess PEG-dialdehyde derivative is then washed away and bound PEG-dialdehyde with one available aldehyde group is reacted with some other molecule such as a peptide or protein.

Independently, the above described PEG-aldehyde derivatives, either type I or II, can also be utilized for the preparation of many other useful PEG derivatives. Thus, by reacting PEG-aldehyde derivatives prepared as disclosed above with a large excess of hydrazine in dimethyl sulfoxide (DMSO) at room or elevated temperature in the presence of reducing agent, PEG-hydrazine derivatives of the formula:

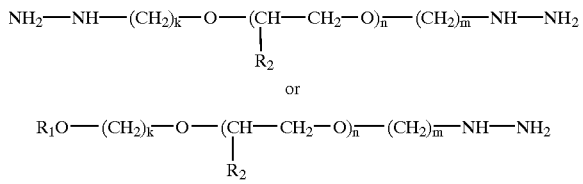

wherein $R_1$ represents lower alkyl, $R_2$ represents lower alkyl or H, n is an integer from about 3 to about 500, and k and m are integers from about 2 to about 12, can be synthesized. A resulting PEG-hydrazine derivative is purified by precipitation with excess ether and recovered by filtration or centrifugation. The completion of the coupling reaction is confirmed by FTIR spectroscopy through the absence of CHO specific bands.

In parallel, by reacting PEG-aldehyde derivatives, prepared as described above, with a large excess of aminoalkylmercaptans of the formula $NH_2$—$(CH_2)_p$—SH, wherein p is an integer from about 2 to about 12, in DMSO, dimethylformamide (DMF), tetrahydrofuran (THF), or dioxane at room or elevated temperature in the presence of reducing agent, PEG-thiol derivatives of the formula:

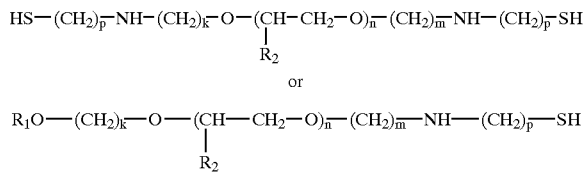

wherein $R_1$ represents lower alkyl, $R_2$ represents lower alkyl or H, n is an integer from about 3 to about 500, and k, m, and p are integers from about 2 to about 12, can be prepared. A resulting PEG-thiol derivative is purified by precipitation in excess of ether and recovered by filtration or centrifugation. The completion of the reaction is confirmed by FTIR spectroscopy through the absence of CHO-specific bands. Further, SH-group content is determined by thiol titration with dipyridyl disulfide at 343 nr by UV spectroscopy.

Also, branched PEG derivatives can be synthesized starting from type I PEG-aldehyde derivatives, as specified above, and diaminocarboxylic acids such as ornithine or lysine at room or elevated temperature in the presence of reducing agent in the appropriate solvent having the formula:

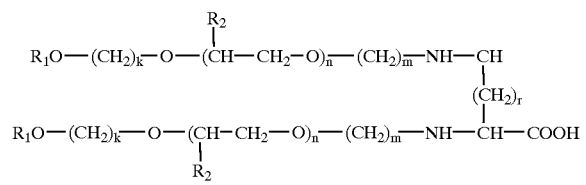

wherein $R_1$ represents lower alkyl, $R_2$ represents lower alkyl or H, n is an integer from about 3 to about 500, k and m are integers from about 2 to about 12, and r is an integer from 0 to about 5. The relative configuration of two amino groups and a carboxylic group in diaminocarboxylic acid can be different from that shown in the formula above. A branched PEG derivative is purified by precipitation in excess ether and recovered by filtration. The completion of the reaction is confirmed by FTIR spectroscopy through the absence of CHO specific bands. Moreover, residual primary amino group content in the preparation is determined by TNBS assay (R. Fields, 25 Methods Enzymol. 464–468 (1972)). Such branched PEG derivatives having a single terminal carboxylic group can be activated through the attachment of N-hydroxysuccinimide to this carboxyl group, thus forming an active ester. Such N-hydroxysuccinimide ester of a particular branched PEG derivative can then be reacted with a selected peptide or protein at pH 7.0–9.0 in aqueous buffer to prepare a particular branched PEG-peptide or PEG-protein conjugate as described in the open literature (R. Clark et al., 271 J. Biol. Chem. 21969–210977 (1996); C. Manfardini et al., 6 Bioconjugate Chem. 62–69 (1995)). This specific modification procedure will make the protein conjugate more basic as compared to native protein (one lysine &-amino group is discharged by amide bond formation but two secondary amino groups are introduced instead), and will thus increase its solubility at pH 7.4 even without taking into account the solubilizing effect of the attached PEG chains.

Also, amino-PEG derivatives can be synthesized starting from type I or type II PEG-aldehyde derivatives, as specified above, and 10 molar excess of ammonium acetate or ammonium chloride at room or elevated temperature in the presence of base such as KOH in methanol. After stirring for 1 hour or less, reducing agent such as $NaBH_3CH$ or $NaBH_4$ (also dissolved in methanol) is added, as described for classical polyethylene glycol aldehydes by J. M. Harris et al., 22 J. Polym. Sci. Polym. Chem. Edn. 341–352 (1984). The resulting amino-PEG derivatives have the formula:

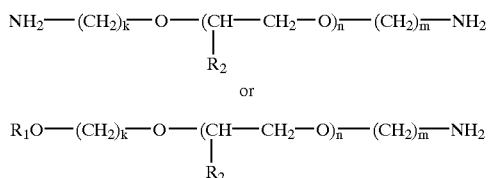

wherein $R_1$ represents lower alkyl $R_2$ represents lower alkyl or H, n is an integer from about 3 to about 500, and k and m are integers from about 3 to about 12. A resulting amino-PEG derivative is purified by precipitation in excess ether and recovered by filtration or centrifugation. The completion of the reaction is monitored by FTIR through the absence of CHO specific bands. Further, primary amino group content in the resulting amino-PEG derivative is determined by TNBS assay. These amino-PEG derivatives, especially those having one $R_1O$ end group, can be reacted with succinic or glutaric anhydride yielding succinamido-carboxyl or glutaramido- carboxyl PEG derivatives. The introduced carboxylic group can be activated by some of the well-known methods in the art, such as conversion to an acid chloride, R. T. Morrison & R. N. Boyd, Organic Chemistry 590, 601 ($3^{rd}$ ed., 1973), and such activated carboxyl-PEG derivatives can be reacted with a particular peptide or protein to prepare a particular PEG derivative-peptide or PEG-derivative-protein conjugate of the formula:

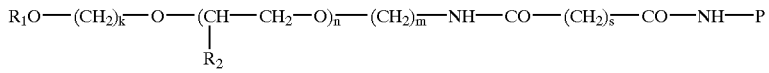

wherein $R_1$ represents lower alkyl, $R_2$ represents lower alkyl or H, n is an integer from about 3 to about 500, k and m are integers from about 2 to about 12, s is 2 or 3, and P is a protein or peptide. The number of PEG derivative chains coupled to a protein or peptide molecule can vary depending on the number of lysine ε-amino groups available and protein/PEG-derivative molar ratio in the modification reaction. Alternatively, such activated carboxyl-PEG derivatives can be reacted with a diaminocarboxylic acids as specified above to prepare branched PEG derivatives of the formula:

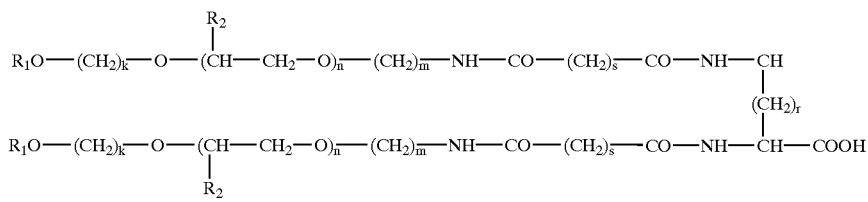

wherein $R_1$ represents lower alkyl, $R_2$ represents lower alkyl or H, n is an integer from about 3 to about 500, k and m are integers from about 2 to about 12, r is an integer from 0 to about 5, and s is 2 or 3. The relative configuration of two amino groups and a carboxylic group in diaminocarboxylic acid can be different from that shown in the formula above. These branched PEG derivatives can also be used after single carboxylic group activation by some of the well-known methods in the art for the synthesis of branched PEG derivative-peptide or PEG derivative-protein conjugates. Again, the number of branched PEG derivatives attached can vary depending on the number of lysine ε-amino groups available and protein/branched PEG derivative molar ratio in the coupling reaction.

What is claimed is:

1. A method for preparing a PEG aldehyde having the formula:

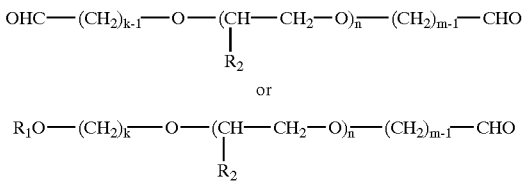

wherein $R_1$ represents lower alkyl, $R_2$ represents lower alkyl or H, n is an integer from about 3 to about 500, and k and m are integers from about 2 to about 12, comprising the steps of:

(a) dissolving a PEG derivative having the formula:

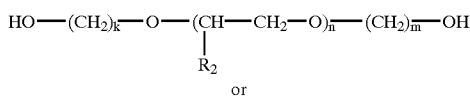

or

-continued $$R_1O-(CH_2)_k-O-(CH(R_2)-CH_2-O)_n-(CH_2)_{\overline{m}}-OH$$

wherein $R_1$ represents lower alkyl, $R_2$ represents lower alkyl or H, n is an integer from about 3 to about 500, and k and m are integers from about 2 to about 12, in an apolar solvent containing 2 equivalents of $K_2CO_3$ for each hydroxyl group to form a mixture;

(b) adding an effective amount of a catalyst and $O_2$ to the mixture, heating at 40–90° C., and incubating for a sufficient period of time for the PEG derivative to be oxidized to the PEG aldehyde;

(c) removing the catalyst; and (d) recovering the PEG aldehyde.

2. The method of claim 1 wherein said apolar solvent is toluene.

3. The method of claim 1 wherein said apolar solvent is benzene.

4. The method of claim 1 wherein said catalyst comprises (i) a transition metal cation having two main oxidative states, (ii) an aromatic heterocycle containing nitrogen, and (iii) a member selected from the group consisting of diethylazodicarboxylate, a hydrazine derivative of diethylazodicarboxylate, and tert-butyl analogs thereof.

5. The method of claim 4 wherein said transition metal cation having two main oxidative states is a member selected from the group consisting of $Cu^+$, $Co^{2+}$, $Fe^{2+}$, $Ni^{2+}$, and mixtures thereof.

6. The method of claim 5 wherein said transition metal cation having two main oxidative states is $Cu^+$.

7. The method of claim 4 wherein said aromatic heterocycle containing nitrogen comprises 1,10-phenanthroline.

8. The method of claim 4 wherein said aromatic heterocycle containing nitrogen comprises α,α'-dipyridyl.

9. The method of claim 4 wherein said member selected from the group consisting of diethylazodicarboxylate, a hydrazine derivative of diethylazodicarboxylate, and tert-butyl analogs thereof is diethylazodicarboxylate.

10. The method of claim 4 wherein said catalyst comprises CuCl, 1,10-phenanthroline, and diethylazodicarboxylate.

11. The method of claim 1 wherein said effective amount of catalyst comprises about 1 to about 10 mol %.

12. The method of claim 11 wherein said effective amount of catalyst comprises about 5 mol %.

* * * * *